(12) United States Patent
Smith et al.

(10) Patent No.: US 6,997,914 B2
(45) Date of Patent: Feb. 14, 2006

(54) IMPLANTABLE ACCESS PORT

(75) Inventors: David A. Smith, Ellerslie, GA (US);
Michael Fowler, Fayetteville, GA (US)

(73) Assignee: Horizon Medical Products, Inc., Manchester, GA (US)

( * ) Notice: Subject to any disclaimer, the term of this patent is extended or adjusted under 35 U.S.C. 154(b) by 440 days.

(21) Appl. No.: 10/114,343

(22) Filed: Apr. 2, 2002

(65) Prior Publication Data
US 2003/0130627 A1    Jul. 10, 2003

Related U.S. Application Data

(60) Provisional application No. 60/281,184, filed on Apr. 2, 2001.

(51) Int. Cl.
- A61M 5/00 (2006.01)
- A61M 25/00 (2006.01)
- A61M 11/16 (2006.01)

(52) U.S. Cl. ............ 604/288.04; 604/533; 604/180; 604/175

(58) Field of Classification Search ........... 604/288.04, 604/891.1, 523, 244, 288.02, 288.03, 267, 604/533, 175, 180, 502; 606/80
See application file for complete search history.

(56) References Cited

U.S. PATENT DOCUMENTS

| | | | |
|---|---|---|---|
| 4,405,305 A * | 9/1983 | Stephen et al. | 604/502 |
| 4,425,119 A | 1/1984 | Berglund | 604/175 |
| 4,645,495 A | 2/1987 | Vaillancourt | 604/180 |
| 4,673,394 A | 6/1987 | Fenton, Jr. et al. | 604/175 |
| 4,710,174 A | 12/1987 | Moden et al. | 604/175 |
| 4,767,410 A | 8/1988 | Moden et al. | 604/175 |
| 4,778,452 A | 10/1988 | Moden et al. | 604/93 |
| 4,781,695 A * | 11/1988 | Dalton | 604/175 |
| 4,822,341 A | 4/1989 | Colone | 604/175 |
| 4,886,501 A | 12/1989 | Johnston et al. | 604/175 |
| 4,955,861 A | 9/1990 | Enegren et al. | 604/141 |
| 4,983,162 A | 1/1991 | Metais et al. | 604/43 |
| 5,041,098 A | 8/1991 | Loiterman et al. | 604/175 |
| 5,092,849 A | 3/1992 | Sampson | 604/175 |
| 5,178,612 A | 1/1993 | Fenton, Jr. | 604/283 |
| 5,213,574 A | 5/1993 | Tucker | 604/93 |
| D337,637 S | 7/1993 | Tucker | D24/111 |
| 5,263,930 A * | 11/1993 | Ensminger | 604/288.03 |
| 5,281,205 A * | 1/1994 | McPherson | 604/267 |

(Continued)

Primary Examiner—Kevin C. Sirmons
Assistant Examiner—Roz Maiorino
(74) Attorney, Agent, or Firm—Needle & Rosenberg, P.C.

(57) ABSTRACT

An implantable access port for use in transferring a fluid transdermally between an external fluid storage or dispensing device and a site within a patient's body is disclosed. The access port includes a base, a bowl-shaped reservoir defined within the base by a smooth surfaced wall, and a septum secured to the base and enclosing the reservoir within the base. The access port also includes a reservoir outlet defined centrally within the reservoir. The bowl-shaped reservoir is defined by a continuous smooth-surfaced curvilinear wall. The reservoir may thus be sized and shaped as a parabola, or may be hemispherical or semi-hemispherical in cross-section. The reservoir outlet is defined at a center point on the bottom of the reservoir wall, may be partially or fully recessed within the bottom of the reservoir wall, and is also defined in the base tangentially with respect to the bottom of the reservoir wall. The access port also has an outlet passageway defined within the base and extending in communication with the reservoir outlet and an external opening defined in the exterior of the base.

14 Claims, 5 Drawing Sheets

U.S. PATENT DOCUMENTS

| | | |
|---|---|---|
| 5,318,545 A | 6/1994 | Tucker ............... 604/244 |
| 5,387,192 A | 2/1995 | Glantz et al. ............ 604/93 |
| 5,399,168 A | 3/1995 | Wadsworth, Jr. et al. ... 604/175 |
| 5,520,632 A | 5/1996 | Leveen et al. ............ 604/9 |
| 5,527,307 A | 6/1996 | Srisathapat et al. ...... 604/892.1 |
| 5,558,641 A | 9/1996 | Glantz et al. ............ 604/93 |
| 5,695,490 A | 12/1997 | Flaherty et al. ......... 604/891.1 |
| 5,702,363 A | 12/1997 | Flaherty ............... 604/93 |
| 5,713,844 A | 2/1998 | Peyman ............... 604/9 |
| 5,741,228 A | 4/1998 | Lambrecht et al. ......... 604/93 |
| 5,792,104 A | 8/1998 | Speckman et al. ........ 604/93 |
| 5,810,789 A | 9/1998 | Powers et al. ............ 604/280 |
| 5,830,172 A | 11/1998 | Leveen et al. ............ 604/9 |
| 5,836,935 A * | 11/1998 | Ashton et al. ............ 604/891.1 |
| 5,840,063 A | 11/1998 | Flaherty ............... 604/93 |
| 5,951,512 A * | 9/1999 | Dalton ............... 604/288.04 |
| 5,957,890 A | 9/1999 | Mann et al. ............ 604/131 |
| 5,989,216 A * | 11/1999 | Johnson et al. ......... 604/288.02 |
| 6,102,884 A | 8/2000 | Squitieri ............... 604/8 |
| 6,213,973 B1 * | 4/2001 | Eliasen et al. ............ 604/93.01 |
| 6,228,088 B1 * | 5/2001 | Miller et al. ............ 606/80 |

* cited by examiner

IMPLANTABLE ACCESS PORT

CROSS-REFERENCE TO RELATED APPLICATIONS

This application claims priority to provisional U.S. Patent Application Ser. No. 60/281,184, filed on Apr. 2, 2001, in the United States Patent and Trademark Office, the provisions of which are incorporated herein fully by this reference.

FIELD OF THE INVENTION

The invention relates in general to medical devices. More particularly, the invention relates to an implantable access port for use in accessing either the vasculature or a selected treatment site within the body of a patient.

BACKGROUND OF THE INVENTION

The use of implantable access ports in the art of drug therapy is well known, in which an access port is implanted beneath the subcutaneous layers of a patient's skin. The known access ports are constructed to provide for repeated access to the vascular system of a patient, or a selected treatment site within the patient's body. The use of these devices reduces the trauma otherwise associated with multiple punctures of the skin, or the inconvenience of an externalized catheter for patient treatment purposes. For example, implantable access ports are used to facilitate frequent blood sampling, or to provide for the delivery of medications, nutritions, blood products, and imaging solutions into the patient's blood stream, or to a desired treatment site within the patient. Access to the implanted device/port is typically accomplished by percutaneous needle insertion through the patient's skin into the access port through a penetrable septum or other similar structure by using a non-coring hypodermic needle.

Implantable access ports are supplied as sterile devices, are provided for single patient use only, and are available in a variety of port materials, including polysoufone, acetal plastic and titanium. Available catheter materials include polyurethane and silicone. Suture holes are typically formed in the access port as a part of the base portion thereof and are used to facilitate the anchorage of the access port to the patient's underlying fascia, for example muscle. Implantable access ports are available in single, dual, and low profile models, and are available with attachable, or attached catheters.

A major problem with implanted vascular access systems, and in particular access ports, is the occlusion of the system by coagulated blood or other material between uses. As known, occlusion occurrences can lead to patient complications such as systemic infection, pocket infection, extravasation of medications, and port failure, all of which may lead to an explant of the device. Further, most patients that receive implantable access ports are either immune compromised, or are in danger of becoming immune compromised. These complications can therefore have a serious effect on the patient. As known, there are clinical steps that can be taken to prevent this occurrence, such as flushing and infusion of the access port with a saline solution. The growth of such occlusive substances, however, occurs through time and appears to occur at a much higher rate in access ports with edges and gaps present in the flow path.

For example, one well known type of access port has a cylindrical reservoir formed within the base of the access port, an example of which is disclosed in U.S. Pat. No. 5,041,098 to Loiterman et al. Although access ports with cylindrical reservoirs have proven to be quite successful and gained wide acceptance and usage as described above, problems do exist with this type of construction. Namely, there are angular corners or junctions formed where the respective side walls of the reservoir join the bottom and top walls, respectively, forming the reservoir, and the outlet passageway is typically defined with the side wall of the reservoir such that it is spaced from (above) the bottom wall or surface of the reservoir. So defined, the outlet/outlet passageway forms a small ledge or catch pocket in the reservoir which may lead to the occlusion of blood or other substances passed into or drawn from out of the access port.

Additionally, access ports with cylindrical reservoirs typically enclose a large amount of space which results in a large volume of fluid that must flow into the access port during use, and which fluid remains in the port thereafter. This extra fluid also reduces the efficiency of flushing protocols by requiring larger flows of fluid over extended times to completely flush the reservoir after use. This is further compounded by the positioning of the outlet passageway at a central location within the reservoir side wall such that a gap exists between the bottom of the reservoir and the entrance to the outlet passageway.

What is needed, therefore, is an implantable access device with an improved reservoir configuration which will further reduce the occurrence of occlusion by improving upon the technology of reservoir designs. Moreover, there is a need for such an improved reservoir design coupled with a more efficient means of draining fluids and other materials from the reservoir of the access port during and after the usage of the port.

SUMMARY OF THE INVENTION

The present invention is an implantable access device for allowing repeated access to, and for use in transferring a fluid transdermally between an external fluid storage or dispensing device and a site, space, device, or other object, fluid, tissue or region within the body of a patient, and which access port overcomes some of the design deficiencies of the known access ports.

In a first embodiment the access port comprises a base, a bowl-shaped reservoir defined within the base by a smooth surfaced wall, a septum secured to the base and enclosing the reservoir therein, and a reservoir outlet defined centrally within the reservoir. The reservoir is defined by a continuous wall, which may further comprise a curvilinear wall. So fashioned, the reservoir may be formed as a parabola with the reservoir outlet defined at the focus of the parabola/reservoir. The reservoir, as desired, may also be hemispherical or semi-hemispherical in shape.

The reservoir outlet is at least partially recessed within the reservoir wall, and may be fully recessed in the reservoir wall and access port base. The reservoir outlet is preferably defined in the bottom of the reservoir wall and at the center thereof, the bottom of the reservoir wall being that portion of the reservoir spaced furthest from an open-face formed by the reservoir/reservoir wall within the base. The access port also includes an outlet passageway defined within the base, the outlet passageway being in communication with the reservoir outlet and extending to, and in communication with an external opening defined in the exterior of the base. The external base opening is further constructed and arranged to be placed in sealed fluid communication with a catheter of known construction, as desired.

In a second embodiment, the access port of the invention comprises a base, a bowl-shaped reservoir defined within the base by a continuous smooth-surfaced wall, and a reservoir outlet defined within the reservoir wall. This embodiment of the access port also includes a septum secured to the base and enclosing the reservoir within the base. The reservoir outlet is defined within the base in the bottom portion of the reservoir wall and is preferably at the bottom center of the reservoir wall.

In yet another embodiment, the access port comprises a base, a reservoir defined within the base, the reservoir having an open face and an opposed bottom, and a reservoir outlet opening defined in the bottom of the reservoir. Once again, the access port may also include a septum secured to the base and enclosing the open face of the reservoir on the base. The reservoir outlet is defined within the base at the center of the reservoir bottom, and is also defined in the base tangentially with respect to the bottom of the reservoir. If desired, the reservoir of the access port may be bowl-shaped, as described above, and thus may be formed by a smooth surfaced wall, which wall may also be a curvilinear wall.

In each of the embodiments of the invention, the reservoir may thus be formed to have a parabolic, hemispherical, or semi-hemispherical shape in cross-section. With the reservoir outlet formed in or at the center of the bowl-shaped reservoir, the smooth flow of material from the reservoir into the outlet and out of the access port is enhanced. Moreover, by positioning the reservoir outlet within the center of the reservoir, essentially the bottom of the continuous reservoir wall, there is no unusable flow space in which the buildup of occluding substances, for example drugs, aspirated blood, and the like, can occur.

Additionally, the design of the reservoir outlet and the reservoir shape and size assure for a more effective reservoir cleansing when the port is flushed with a solution, for example an aqueous saline solution, between uses. The implantable access device of this invention can be thus used for the introduction of therapeutic agents, for the infusion of withdrawal of fluids, or for the introduction of sensing, sampling, or treatment devices to another implanted device, or to body regions within the patient.

DETAILED DESCRIPTION

Figure 1:
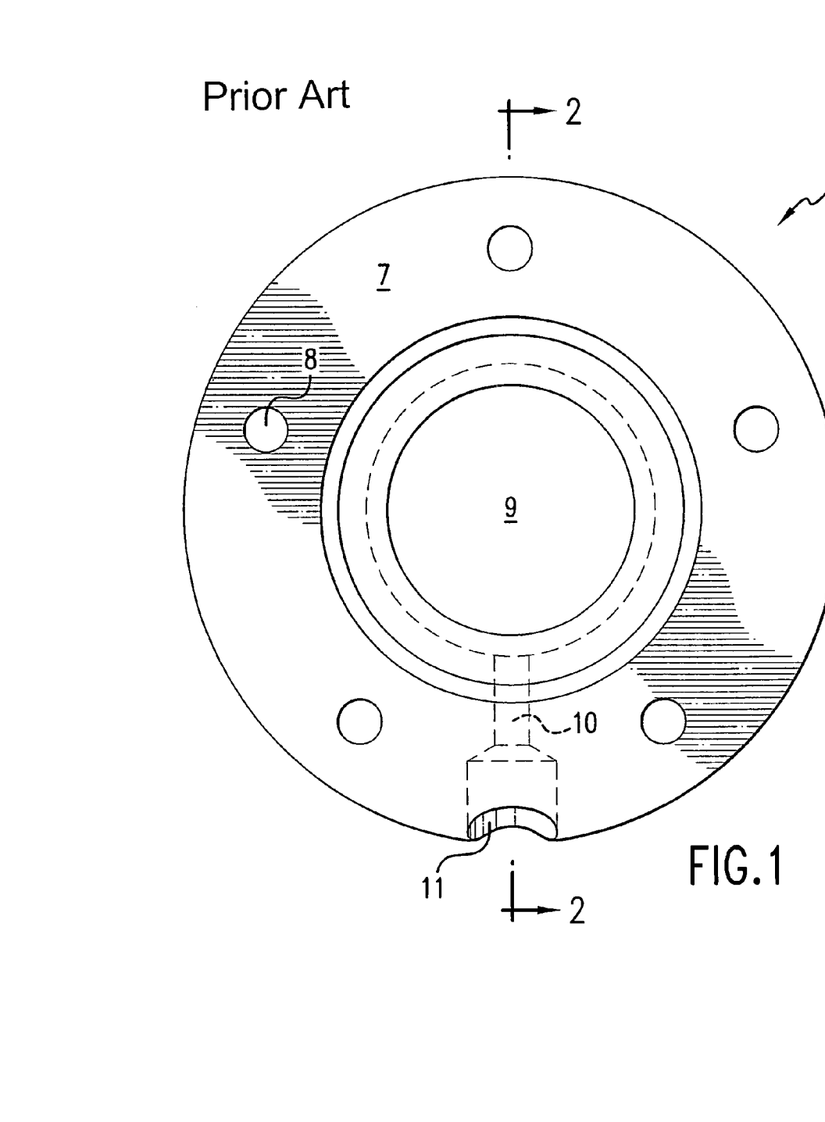
FIG. 1 is a top plan view of a known type of implantable access device having a cylindrical reservoir.
Figure 2:
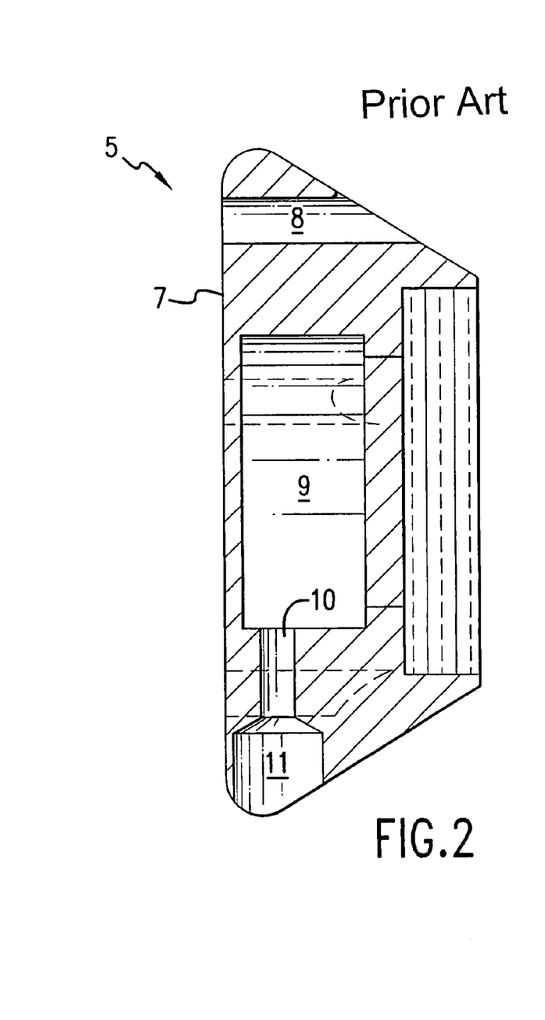
FIG. 2 is a side cross-sectional view along line 2—2 of FIG. 1.
Figure 3:
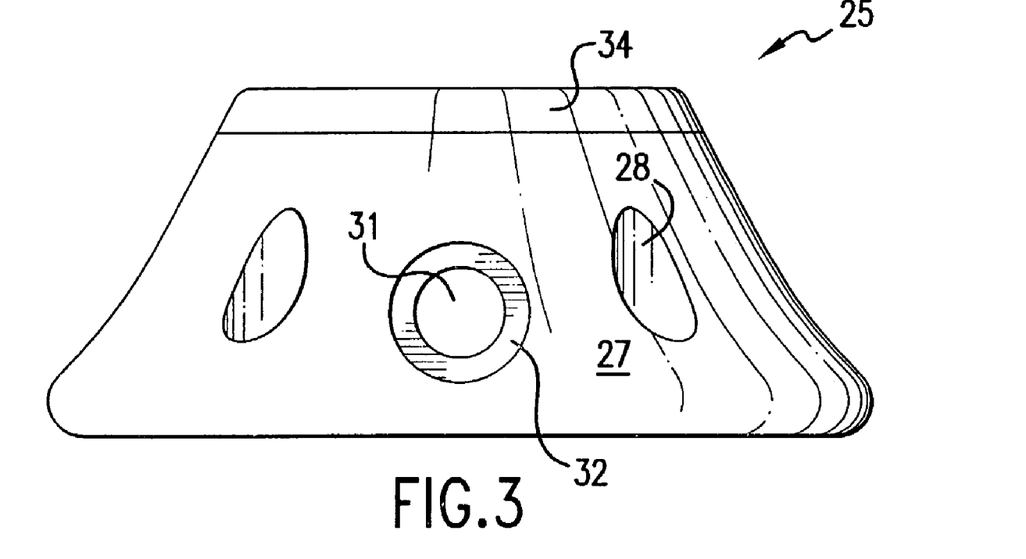
FIG. 3 is side elevational view of a first embodiment of the implantable access device of this invention having a bowl-shaped reservoir provided as a part thereof.

Referring now in detail to the drawings, in which like reference numerals indicate like parts or elements throughout the several views, a known type of an implantable access port 5 is illustrated in FIGS. 1 and 2. The known access port is comprised of a base 7 having a radially spaced series of suture holes 8 defined within the base. So provided, the access port may be sewn to the fascia of a patient by passing appropriate sutures through the suture holes to fasten the access port to the underlying muscle and/or tissues of the patient.

As best shown in FIGS. 1 and 2, the access port 5 here features a cylindrical reservoir 9 formed within and as a part of, the base. An outlet passageway 10 extends radially away from the side wall of the reservoir to an opening 11 defined within the exterior side wall of the base, the outlet passageway being in fluid communication with the reservoir and the exterior opening. Absent in FIGS. 1 and 2 is a penetrable septum of a type known in the art, which septum would be affixed to the open face of the base by a suitable retainer ring (not illustrated).

As shown in FIG. 2, there are a number of angular corners or junctions formed where the respective side walls of the reservoir join the bottom and top walls or surfaces, respectively, forming the cylindrical reservoir. The outlet passageway 10 extends from an opening defined in the side wall of the reservoir such that both the outlet opening and the outlet passageway are spaced from (above) the bottom of the reservoir. So defined, the outlet opening forms a small ledge or catch pocket in the reservoir, which may in turn lead to the occlusion of blood or other substances, respectively, in the reservoir as these fluids are passed into or drawn from out of the access port.

Also, cylindrical reservoirs of the type shown in FIGS. 1 and 2 typically enclose a large amount of space, which results in a large volume of fluid that must flow into the access port during use, and which fluid remains in the port thereafter. This extra fluid reduces the efficiency of flushing protocols by requiring larger flows of fluid over extended times to completely flush the reservoir after use. As described, this is further compounded by the positioning of the outlet step, i.e., the outlet opening and the outlet passageway 10, at a central location within the upstanding reservoir side wall, such that a gap exists between the bottom of the reservoir and the entrance to the outlet passageway.

Figure 4:
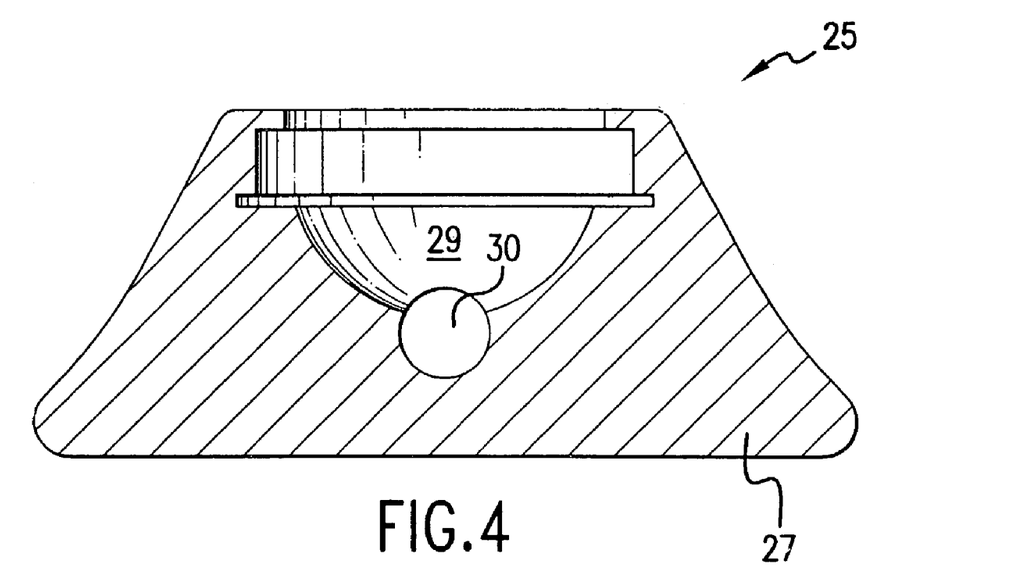
FIG. 4 is an elevational view, in cross section, of the access port of FIG. 3.
Figure 5:
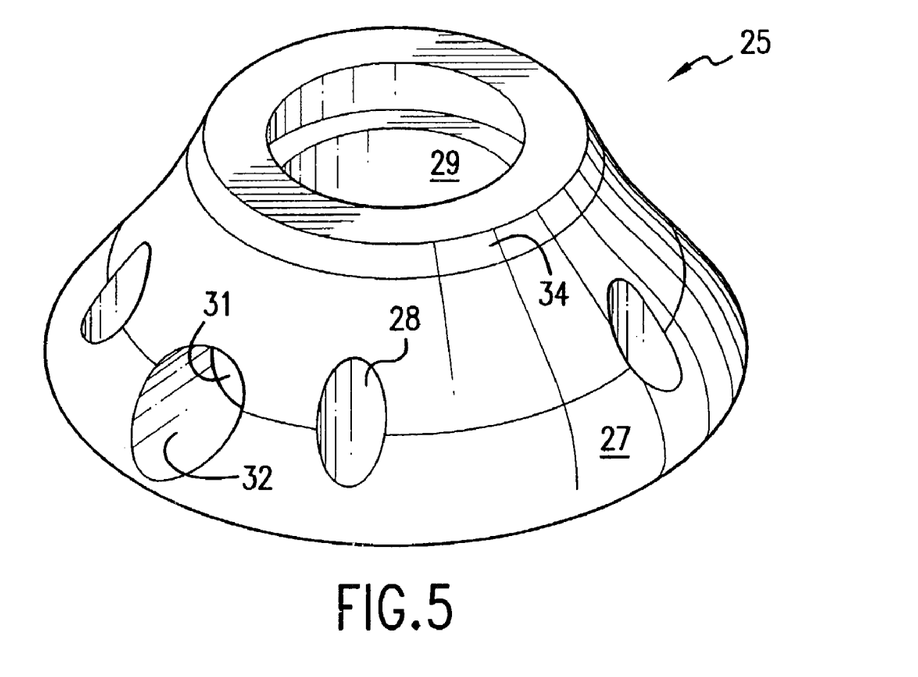
FIG. 5 is a front, side perspective view of the access port of FIG. 3.
Figure 6:
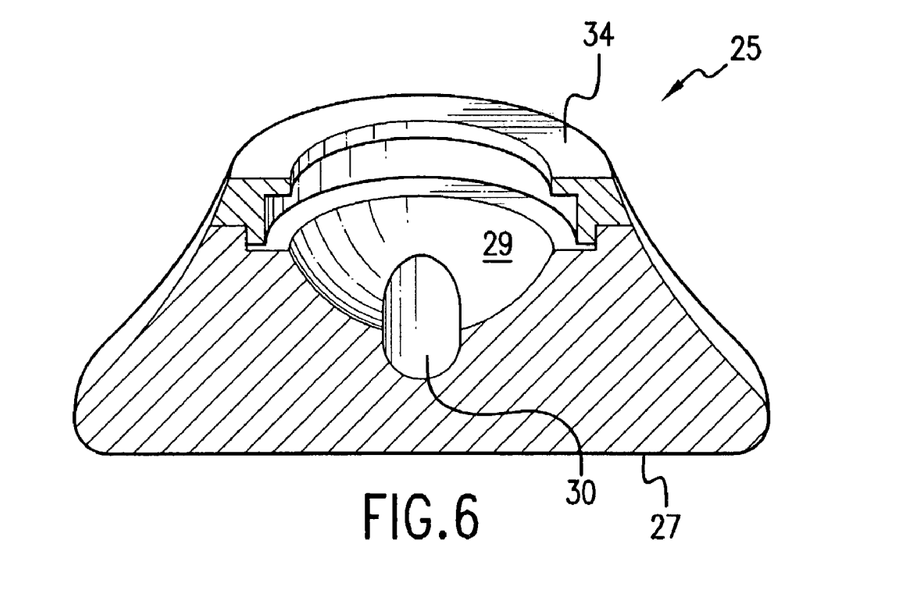
FIG. 6 is a perspective view, in cross section, of the access port of FIG. 3.

A first embodiment of the implantable access port of this invention is illustrated in FIGS. 3 through 6. An implantable access port 25 is illustrated having a base 27 provided with a series of radially spaced suture holes 28, in known fashion. Here, however, in contrast to the known types of access ports, the access port 25 is formed to have a bowl-shaped reservoir 29, as best seen in FIGS. 4 and 6. The bowl-shaped reservoir is defined by a single smooth-surfaced wall which defines an open top of the reservoir, and a focus or center point at the "bottom" or center of the reservoir. The wall of the reservoir thus comprises a continuous curvilinear side wall.

The bowl-shaped reservoir, in all of the embodiments of the present invention, may thus be parabolic in shape, as well as hemispherical or semi-hemispherical when viewed in cross-section. The bowl-shaped formation of the reservoir in the base of the access port in such a manner thus allows for the reservoir to be made with the walls and the floor of the reservoir as one unit, i.e., one continuous wall, without otherwise forming any corners or edges associated with the reservoir at which a buildup of occluding particles could occur.

Still referring to FIGS. 4 and 6, a reservoir outlet 30 is defined within the base of the access port at the center or focus of the bottom of the reservoir. The bottom of the reservoir, as such, is that portion which is opposed to the open face of the reservoir defined in the base. The bottom of the reservoir thus comprises the center or the focus of the reservoir, as that term is understood by those skilled in the art. An outlet passageway 31 is also defined within the base and extends in communication with the reservoir outlet 30 and an external opening 32 defined in the exterior side wall of the access port base.

The placement of the reservoir outlet at the focus or center of the bowl-shaped reservoir enhances the smooth flow of material, i.e., fluids, to include medications and blood, into and out of the reservoir. The reservoir outlet 30 is shown in FIGS. 4 and 6 to be partially recessed, i.e., partially defined or formed within the floor of the reservoir, and is positioned directly in the center of the reservoir so that the outlet, which may also be thought of as a reservoir stem, acts like a drain to remove fluid and particles from the reservoir. Also, and a shown, the reservoir outlet is defined within the base of the access-port so that the reservoir outlet is preferably tangential with respect to the reservoir wall, and particularly with respect to the bottom portion thereof.

The bowl-shaped reservoir thus encloses the minimal amount of space required to allow a hypodermic needle (not illustrated) to access the reservoir through the septum (not illustrated) of the access port. The septum will comprise a penetrable septum of those types well known in the art, and will be secured to the base over the open face of the reservoir by a suitable retainer ring 34 which will be threadably affixed to the base of the access port. The bowl-shaped reservoir of this access port, with its improved reservoir design, thus reduces the likelihood of occlusion occurrences and failures within the access port, and is believed to minimize the likelihood of the above-described patient complications.

Accordingly, as taught herein, the volume of the bowl-shaped reservoir is greatly reduced with respect to access ports having cylindrical access ports, which thus enhances the efficiency of flushing protocols used with the port. For example, it is anticipated that the volume of the bowl-shaped reservoir 29, 129 in FIGS. 3–9, respectively, may be around 0.3 cc's whereas the cylindrical reservoir 9 of the access port 5 (FIGS. 1–2) known in the art may have a volume of approximately 0.6 to 1.0 cc's.

Figure 7:
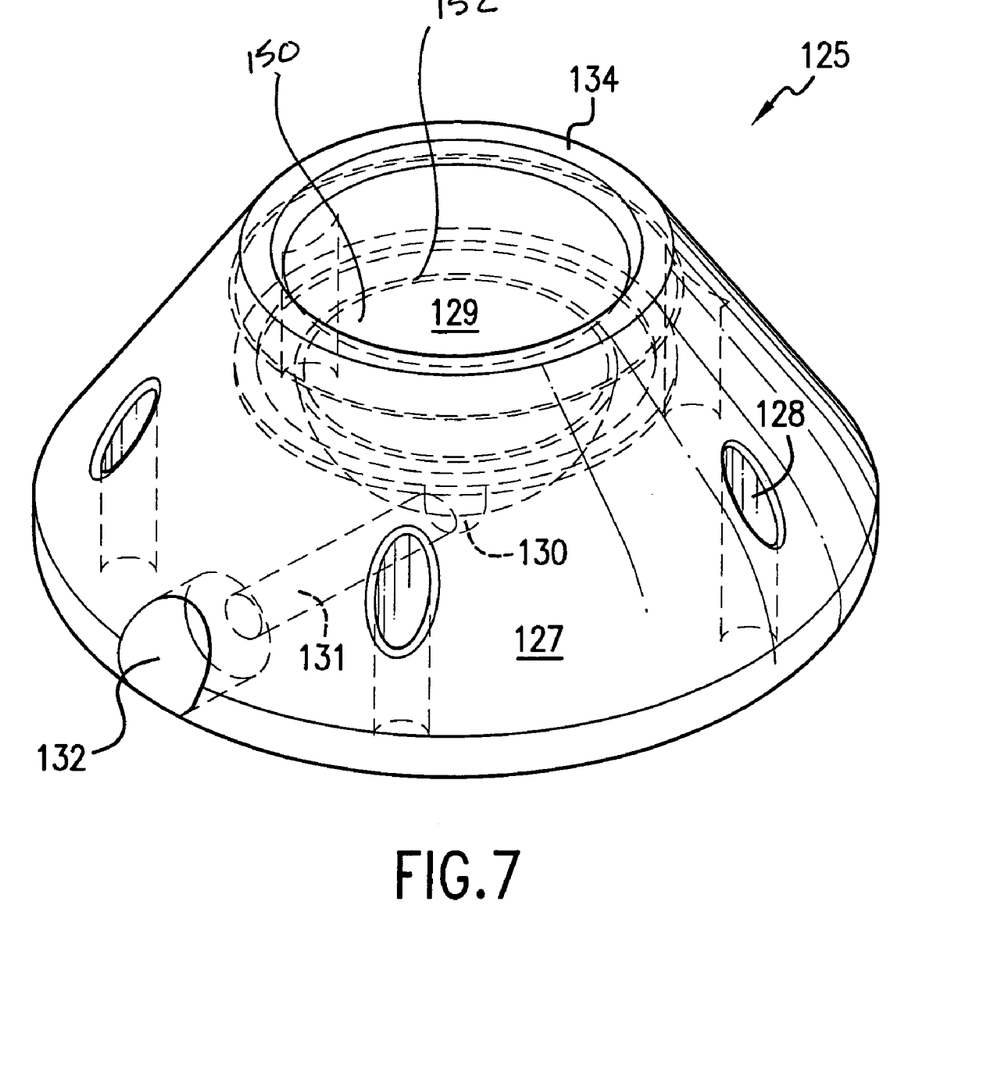
FIG. 7 is a perspective view of a second embodiment of the implantable access device of this invention having a bowl-shaped reservoir.
Figure 8:
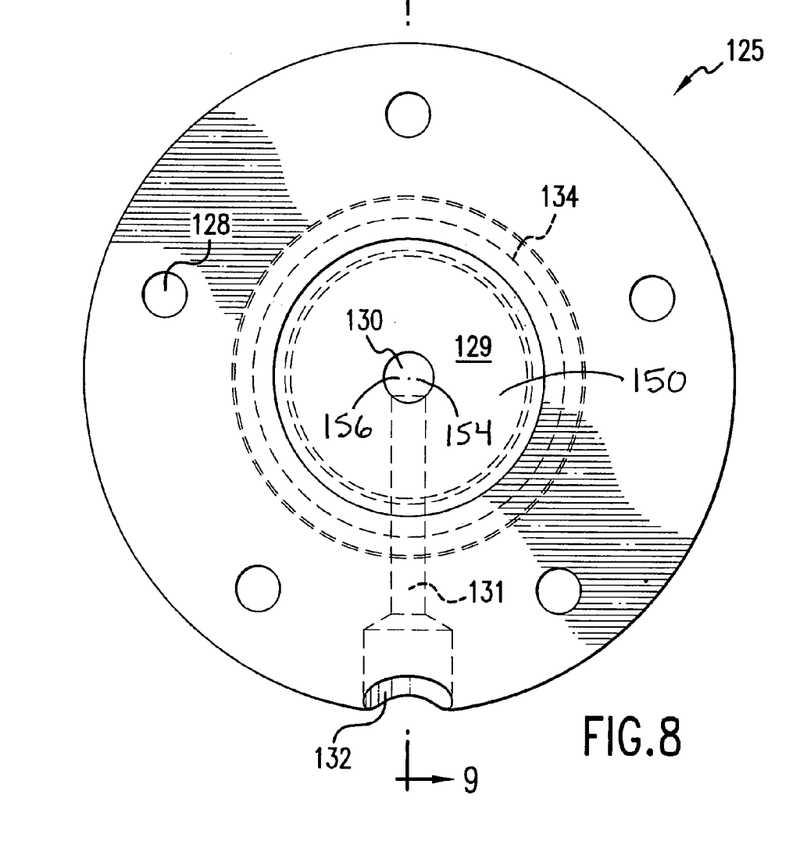
FIG. 8 is top plan view of the implantable access device of FIG. 7.
Figure 9:
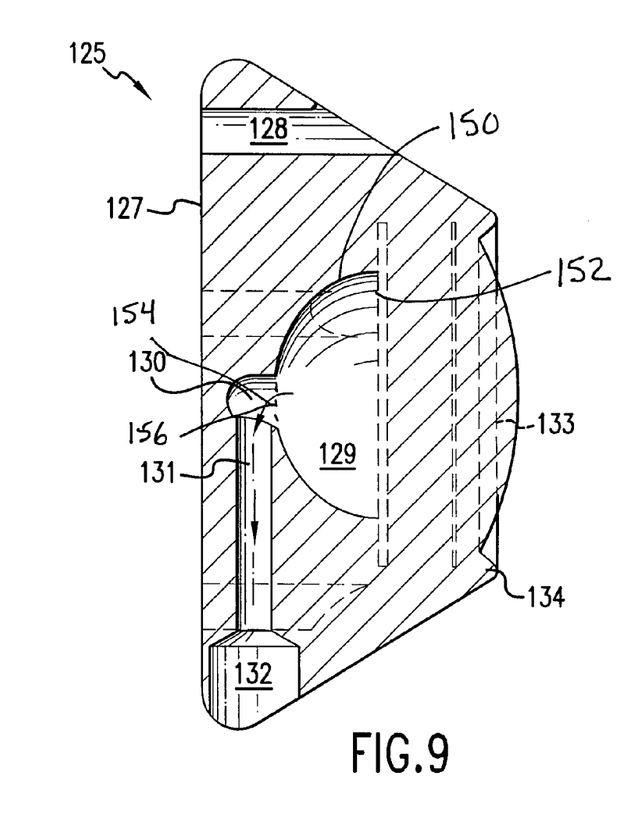
FIG. 9 is side cross-sectional view along line 9—9 of FIG. 8.

A second embodiment of the implantable access port of this invention is illustrated in FIGS. 7 through 9. The implantable access port 125 of FIGS. 7–9 includes a base 127 having a radially spaced series of suture holes 128 defined therein, as known. The suture holes may be filled with a penetrable material, for example an elastomeric material, for otherwise filling the openings within the base in order to limit tissue in-growth into the suture holes or openings.

Still referring to FIGS. 7–9, the access port 125 has a bowl-shaped reservoir 129 defined within and as a part of the base of the access port. As with the reservoir 29 of FIGS. 3–6, the bowl-shaped reservoir 129 is once again defined by a continuous smooth-surfaced wall 150, for example a curvilinear wall, which defines an open top 152 of the reservoir and an opposed bottom 154 having a focus or center point 156 thereat, the bottom or bottom portion 154 of the reservoir once again being that portion of the reservoir opposed to and spaced farthest from the open top or face 152 thereof. The reservoir may thus be parabolic, hemispherical, or semi-hemispherical in shape (cross-section). So fashioned, the reservoir does not provide any corners or associated edges at which a buildup of occluding particles or substances could occur.

A reservoir outlet 130 is defined within the base at the bottom of the bowl-shaped reservoir, and more particularly at the center thereof, and is in communication with an elongate outlet passageway 131 defined within the base and extending in communication with the reservoir outlet to an external opening 132 defined within the exterior side wall of the base. As illustrated, the outlet opening may best be thought of as an outlet stem extending from the center or focus of the bowl-shaped reservoir. Unlike the outlet opening defined in the embodiment of the access port illustrated in FIGS. 3–6, which is partially recessed within the bottom surface of the reservoir wall (FIG. 4), here the reservoir outlet 130 is fully recessed in the base with respect to the bottom, center of the reservoir, as best shown in FIGS. 8 and 9 for forming a more discrete reservoir drain.

Referring to FIG. 9, the access port 125 is provided with a penetrable septum 133 of known construction, the septum being secured on the base of the access port by a retainer ring 134 threadably affixed to the base. The manner of fabrication, and materials used in the construction of the implantable access ports 25 and 125 of this invention, respectively, are as described in U.S. Pat. Nos. 4,673,394, and 5,951,512, each of which is assigned to Horizon Medical Products, Inc. of Manchester, Ga., and each of which is fully incorporated herein by this reference.

As such, the penetrable septums of the preferred embodiments of this invention are comprised of a self-resealing polymer, which is preferably an elastomer, such as silicon rubber or a latex, and which is adapted to permit access using a hypodermic needle (not illustrated) into the reservoir formed within the respective access ports. The respective bases 27, and 127, and the retainer rings 34, 134, are each preferably comprised of a biocompatible material, such as electropolished stainless steel, or other surgical grades of steel, to also include a biocompatible hard material such as titanium. Additionally, the access port, with the exception of the septum, can be manufactured of a suitable plastic material intended for implantation within a human body, and approved for use therefor. Also, the base of the access port, in association with the external opening defined in the side wall of the base, for all embodiments of the inventive access port, are provided with a catheter mount of known construction, which for example, may comprise the locking type of catheter mount illustrated in the No. 394 patent to Fenton et al., the teaching of which has been incorporated herein by reference.

The bowl-shaped reservoir allows for an entirely smooth geometry in the reservoir in that the reservoir wall does not have any corners or edges that may catch materials or substances which might otherwise settle on or occlude at least a portion of the reservoir or reservoir outlet. The placement of the respective outlets 30, 130, at the bottom or center of the reservoir, preferably tangentially with respect thereto as illustrated in FIG. 9, and either partially or fully recessed in the base with respect to the reservoir bottom, further prevents the formation of any "dead space" which would otherwise allow the buildup of particles which may lead to occlusion of the access port. The bowl-shaped reservoir of this access port, therefore, with its improved reservoir design, reduces the likelihood of these types of occlusion occurrences and failures, and is believed to minimize the likelihood of the above-described patient complications.

Although several embodiments of the invention have been disclosed in the foregoing specification, it is understood by those skilled in the art that many modifications and other embodiments of the invention will come to mind to which the invention pertains, having the benefit of the teaching presented in the foregoing description and associated drawings. It is thus understood that the invention is not limited to the specific embodiments disclosed hereinabove, and that many modifications and other embodiments are intended to be included within the scope of the invention. Moreover, although specific terms are employed herein, they are used only in a generic and descriptive sense, and not for the purposes of limiting the described invention.

We claim:

1. An implantable access port for use in transferring a fluid transdermally between an external fluid storage or dispensing device and a site within a patient's body, said access port comprising:
    a base;
    a bowl-shaped reservoir defined within the base by a smooth surfaced wall, the bowl-shaped reservoir having an open top and an opposed bottom portion, wherein a center of the bottom portion of the bowl-shaped reservoir is spaced farthest from the open top, wherein the bowl-shaped reservoir has a cross-sectional shape selected from a group consisting of: a parabolic shape, a hemispherical shape, and a semi-hemispherical shape;
    a septum secured to the base and enclosing the reservoir within the base;
    a reservoir outlet defined within the base and forming an outlet stem, the reservoir outlet underlying the center of the bottom portion of the bowl-shaped reservoir, wherein at least a portion of the reservoir outlet extends outwardly away from the wall of the bowl-shaped reservoir and away from the center of the reservoir, and wherein the reservoir outlet defines an opening positioned substantially tangent with respect to the center of the bottom portion of the reservoir; and
    an outlet passageway defined within the base, the outlet passageway being in communication with an external opening defined in an exterior side wall of the base and the opening in the reservoir outlet.

2. The access port of claim 1, the reservoir being defined by a single continuous wall.

3. The access port of claim 2, the reservoir being defined by a curvilinear wall.

4. The access port of claim 1, wherein the center of the bottom portion of the bowl-shaped reservoir is defined at the focus of the parabolic cross-sectional reservoir; and wherein the reservoir outlet is defined at the focus.

5. The access port of claim 1, the reservoir outlet being at least partially recessed within the reservoir wall.

6. The access port of claim 1, the reservoir outlet being fully recessed within the reservoir wall.

7. The access port of claim 1, the reservoir outlet being defined at the center of the reservoir wall.

8. The access port of claim 1, the reservoir outlet being defined at a bottom portion of the reservoir wall spaced furthest from an open-face formed by the reservoir wall within the base.

9. The access port of claim 8, the reservoir outlet being defined at the center of the reservoir wall.

10. The access port of claim 8, the reservoir outlet being defined in the base tangentially with respect to the bottom portion of the reservoir wall.

11. The access port of claim 1, wherein the outlet passageway extends substantially tangent with respect to the center of the bottom portion of the reservoir.

12. The access port of claim 11, the external base opening being constructed and arranged to be placed in sealed fluid communication with a catheter.

13. The access port of claim 1, wherein the base of the access port is comprised of a biocompatible material.

14. The access port of claim 1, wherein the septum of the access port is comprised of an elastomeric material.

* * * * *